Figure 1:
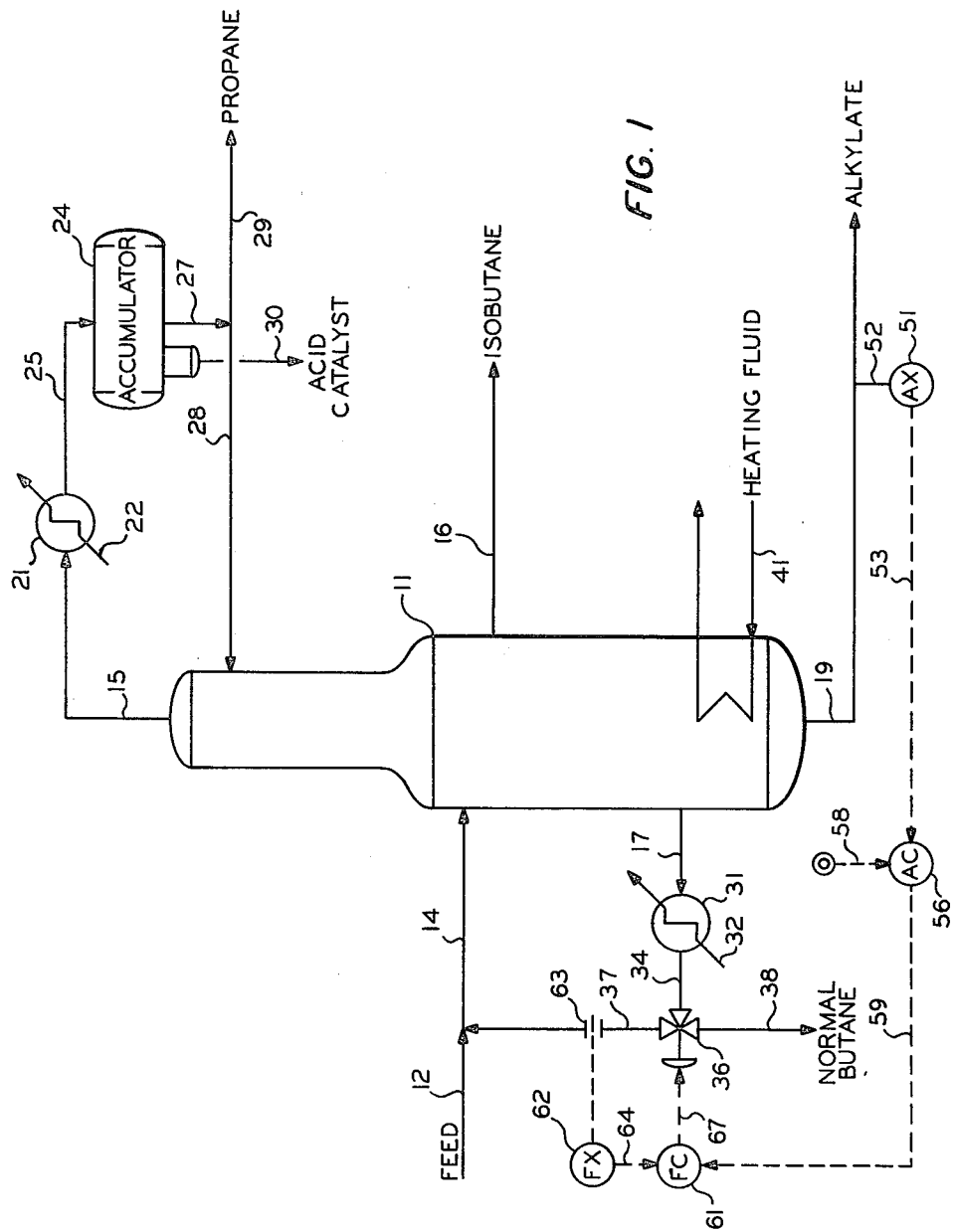

United States Patent [19]

Hutson, Jr.

[11] Patent Number: 4,470,879
[45] Date of Patent: Sep. 11, 1984

[54] FRACTIONATOR CONTROL IN AN ALKYLATION PROCESS

[75] Inventor: Thomas Hutson, Jr., Bartlesville, Okla.

[73] Assignee: Phillips Petroleum Company, Bartlesville, Okla.

[21] Appl. No.: 359,969

[22] Filed: Mar. 19, 1982

[51] Int. Cl.³ .................... B01D 3/42; C07C 2/56
[52] U.S. Cl. .......................... 203/3; 203/98; 203/DIG. 19; 202/160; 585/701; 585/709
[58] Field of Search .................. 203/98, 99, DIG. 19, 203/3; 196/132, 141; 585/956, 701, 709, 719, 723; 62/21, 37, 41; 202/160

[56] References Cited

U.S. PATENT DOCUMENTS

| | | | |
|---|---|---|---|
| 2,342,364 | 2/1944 | Parker | 585/719 |
| 2,442,666 | 6/1948 | Skinner et al. | 585/706 |
| 2,818,459 | 12/1957 | Gantt | 585/719 |
| 2,974,182 | 3/1961 | Van Pool | 203/2 |
| 2,990,437 | 6/1961 | Berger | 585/701 |
| 3,002,818 | 10/1961 | Berger | 585/701 |
| 3,080,438 | 3/1963 | Sailors | 585/701 |
| 3,209,051 | 9/1965 | Bauer et al. | 585/331 |
| 3,212,997 | 10/1965 | Walker | 196/132 |
| 3,253,054 | 5/1966 | Van Pool | 585/712 |
| 3,259,554 | 7/1966 | Constantikes | 203/3 |
| 3,957,901 | 5/1976 | Chapman | 585/701 |
| 4,073,823 | 2/1978 | Vora | 585/719 |
| 4,371,426 | 2/1983 | DiBiano et al. | 203/3 |

Primary Examiner—Wilbur L. Bascomb, Jr.
Assistant Examiner—V. Manoharan
Attorney, Agent, or Firm—French and Doescher

[57] ABSTRACT

Normal butane withdrawn from the main fractionator in an acid alkylation process is recycled to the main fractionator as required to insure that the actual alkylate to normal butane ratio in the alkylate product withdrawn from the main fractionator does not go below a desired ratio. Maintenance of the actual ratio at or above the desired ratio substantially minimizes the concentration of isobutane in the alkylate product stream.

6 Claims, 1 Drawing Figure

FRACTIONATOR CONTROL IN AN ALKYLATION PROCESS

This invention relates to control of the main fractionator in an alkylation process. In one aspect, this invention relates to method and apparatus for substantially minimizing the amount of isoparaffin which is contained in the alkylate product stream which is withdrawn from the main fractionator in an alkylation process.

Alkylation is a process to combine at least one isoparaffin such as isobutane with an olefin such as propylene, butylenes or amylenes to produce a liquid with superior stability and antiknock quality suitable for blending aviation gasoline and motor fuel. An acid catalyst such as hydrofluoric (HF) acid or sulfuric acid serves to catalyze the reaction.

The isoparaffin commonly alkylated is isobutane although isopentane could be utilized if desired. The most commonly used olefins are propylene and butylenes with amylenes being used less frequently. As used herein the term butylenes refers to 1-butene, cis-2-butene, trans-2-butene, and isobutylene. As used herein the term amylenes refers to all of the five carbon olefins. Some propane and normal butane will also generally be present with the propylene and butylenes, and some propane may be produced in the alkylation.

The effluent removed from the alkylation reactor will generally contain alkylate, acid catalyst, isobutane, normal butane and propane. Generally, most of the acid catalyst is removed from this effluent and the remaining mixture is provided as a feed to the main fractionator in the alkylation process. Other components may be present in the feed to the main fractionator but will not be considered in the following discussion since such other components do not play a part in the description of the present invention.

The main fractionator is utilized to separate the alkylate, normal butane, isobutane and propane contained in the feed to the main fractionator. In general, propane is removed as an overhead vapor stream, isoparaffins and normal butane are removed separately as side draw streams and alkylate is removed from the main fractionator as a bottom stream.

From an economic standpoint, it is important to minimize the presence of isobutane in the alkylate stream withdrawn from the main fractionator. Isobutane withdrawn as a side draw stream from the fractionator is recycled to the alkylation reactor but isobutane contained in the alkylate stream is lost to the alkylation process which is undesirable from an economic standpoint.

It is thus an object of this invention to provide method and apparatus for substantially minimizing the amount of isobutane which is contained in the alkylate stream withdrawn from the main fractionator in an alkylation process.

In accordance with the present invention, method and apparatus are provided whereby normal butane withdrawn from the main fractionator is recycled to the main fractionator as required to insure that the actual alkylate to normal butane ratio in the alkylate product withdrawn from the main fractionator does not go below a desired ratio. Maintenance of the actual ratio at or above the desired ratio substantially minimizes the concentration of isobutane in the alkylate product stream.

Other objects and advantages of the invention will be apparent from the foregoing brief description of the invention and the claims as well as the detailed description of the drawing, which is briefly described as follows:

FIG. 1 is a diagrammatic illustration of the main fractionator in an alkylation process with an associated control system.

The invention is illustrated and described in terms of a specific fractionator in an alkylation process in which isobutane is the isoparaffin used. However, the invention is applicable to any fractionator in an alkylation process where it is desired to substantially minimize the presence of isobutane in the alkylate product withdrawn from the fractionator.

A specific control system configuration is set forth in FIG. 1 for the sake of illustration. However, the invention extends to different types of control system configurations which accomplish the purpose of the invention. It is particularly noted that the present invention lies in the recycling of normal butane so as to substantially minimize the presence of isobutane in the alkylate product. The preferred technique for controlling the recycle of normal butane is illustrated in FIG. 1. However, other techniques could be utilized such as an analysis of the feed flowing to the fractionator. The invention extends to any control system which may be utilized to control the recycle of normal butane to the main fractionator so as to substantially minimize the presence of isobutane in the alkylate product.

Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

The controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

Referring now to FIG. 1, there is illustrated a fractional distillation column 11. A feed stream containing alkylate, isobutane, normal butane, acid catalyst and propane is provided through the combination of conduit means 12 and 14 to the fractionator 11. Propane is removed as an overhead vapor stream from the fractional distillation column 11 through conduit means 15. Isobutane is removed as a vapor draw from the fractional distillation column 11 through conduit means 16 and is typically recycled to the alkylation reactor. Normal butane is removed as a vapor draw from the fractional distillation column 11 through conduit means 17. Alkylate is removed as a bottoms product stream from the fractional distillation column 11 through conduit means 19. It is noted that, while the above-described streams will principally contain the constituent mentioned, each of the streams will generally contain impurities and specifically the alkylate stream will contain some normal butane.

The overhead stream flowing through conduit means 15 is provided from the fractional distillation column 11 to the heat exchanger 21. The heat exchanger 21 is provided with a cooling medium through conduit means 22. The at least partially condensed fluid stream from the heat exchanger 21 is provided to the overhead accumulator 24 through conduit means 25. A first portion of the fluid in the overhead accumulator 24 is provided through the combination of conduit means 27 and 28 as an external reflux to the fractional distillation column 11. A second portion of the fluid in the accumulator 24 is removed through the combination of conduit means 27 and 29 as the overhead product.

It is also noted that any acid catalyst remaining in the feed stream flowing through conduit means 14 will generally be removed in the overhead stream. This acid catalyst is removed from accumulator 24 through conduit means 30.

Normal butane flowing through conduit means 17 is provided from the fractional distillation column 11 to the heat exchanger 31. The heat exchanger 31 is provided with a cooling medium through conduit means 32. The condensed normal butane flowing through conduit means 34 is provided through the three-way control valve 36 to either conduit means 37 or conduit means 38. Normal butane flowing through conduit means 37 is combined with the feed flowing through conduit means 12 and is thus recycled through conduit means 14 to the fractional distillation column 11.

Heat is provided to the fractional distillation column 11 by passing a heating fluid through conduit means 41. It is noted that while this is a typical means for supplying heat to a fractional distillation column, other techniques such as recycling a portion of the bottoms stream through a heat exchanger could be utilized if desired.

The fractional distillation process described to this point is conventional with the exception of the recycling of normal butane to the fractional distillation column 11. Additional equipment such as pumps, additional heat exchangers, additional control components, etc., which would typically be associated with a fractional distillation column in an alkylation process have not been illustrated since these additional components play no part in the description of the present invention. It is particularly noted that only those control elements preferably utilized to control the recycle of normal butane to the fractional distillation column 11 are illustrated. Typically, other control elements such as level control for the flow of the alkylate product, control of the reflux flowing through conduit means 28 or control of the heat input to the fractional distillation column would also be utilized.

Analyzer transducer 51, which is preferably a Model 102 process chromatograph manufactured by Applied Automation, Inc., Bartlesville, Okla., is in fluid communication with conduit means 19 through conduit means 52. The analyzer transducer 51 analyzes a sample of the alkylate product flowing through conduit means 19 to determine the concentration of alkylate and the concentration of normal butane. The analyzer transducer 51 provides an output signal 53 which is representative of the actual alkylate to normal butane ratio in the alkylate product flowing through conduit means 19. Signal 53 is provided from the analyzer transducer 51 as the process variable input to the analyzer controller 56.

The analyzer controller 56 is provided with a set point signal 58 which is representative of the desired alkylate to normal butane ratio in the alkylate product flowing through conduit means 19. This desired ratio is chosen so as to substantially minimize the presence of isobutane in the alkylate product. In general, the normal butane acts as a buffer between the alkylate and the isobutane because its boiling point is between the initial boiling point of the alkylate and the boiling point of the isobutane. It has been found that the percentage of normal butane in the alkylate product flowing through conduit means 19 should be in the range of about 3 volume percent to about 7 volume percent based on the total volume of the alkylate product stream flowing through conduit means 19 with a concentration of about 5 volume percent being preferred to substantially minimize the presence of isobutane in the alkylate product stream. A concentration of normal butane in the alkylate product stream of about 3 volume percent corresponds to an alkylate to normal butane volume ratio of about 32:1. In like manner, a concentration of 5 volume percent normal butane corresponds to an alkylate to normal butane volume ratio of about 19:1 and a concentration of about 7 volume percent corresponds to an alkylate to normal butane volume ratio of about 13:1. Thus, signal 58 is preferably representative of an alkylate to normal butane volume ratio of about 19:1.

In response to signals 53 and 58, the analyzer controller 56 provides output signal 59 which is responsive to the difference between signals 53 and 58. Signal 59 is scaled so as to be representative of the flow rate of normal butane through conduit means 37 required to maintain the actual alkylate to normal butane volume ratio in the alkylate product stream substantially equal to the desired volume ratio represented by signal 58. Signal 59 is provided from the analyzer controller 56 as the set point input to the flow controller 61. This flow rate may be zero if the actual alkylate to normal butane ratio is equal to or above the desired ratio.

Flow transducer 62 in combination with the flow sensor 63, which is operatively located in conduit means 37, provides output signal 64 which is representative of the actual flow rate of normal butane through conduit means 37. Signal 64 is provided from the flow transducer 62 as the process variable input to the flow controller 61. In response to signals 59 and 64, the flow controller 61 provides an output signal 67 which is responsive to the difference between signals 59 and 64.

Signal 67 is scaled so as to be representative of the position of the three-way control valve 36 required to maintain the actual flow rate of normal butane through conduit means 37 substantially equal to the desired flow rate represented by signal 59. Signal 67 is provided from the flow controller 61 to the three-way control valve 36 and the three-way control valve 36 is manipulated in response thereto.

In summary, normal butane is recycled to the fractional distillation column 11 so as to substantially minimize the presence of isobutane in the alkylate product flowing through conduit means 19. It is noted that if sufficient normal butane is present in the feedstream flowing through conduit means 12 to satisfy the desired alkylate to normal butane ratio represented by signals 58, the control will act to shut off the flow of normal butane through conduit means 37. However, if sufficient normal butane is not present in the feed flowing to conduit means 12, the control will act to provide normal butane through conduit means 37 so as to ensure that the ratio represented by signal 58 is maintained.

The invention has been described in terms of a preferred embodiment as illustrated in FIG. 1. Specific components which can be used in the practice of the invention as illustrated in FIG. 1 such as analyzer controller 56, flow controller 61, flow transducer 62, flow sensor 63, and the three-way control valve 36 are each well known, commercially available control components such as are described at length in Perry's Chemical Engineers Handbook, Fourth Edition, Chapter 22, McGraw-Hill.

While the invention has been described in terms of the presently preferred embodiment, reasonable variations and modifications are possible by those skilled in the art and such modifications and variations are within the scope of the described invention and the appended claims.

That which is claimed is:

1. Apparatus comprising:
    a fractional distillation column;
    means for supplying a feed stream containing alkylate, isobutane and normal butane to said fractional distillation column;
    means for removing a bottoms stream containing a substantial portion of the alkylate contained in said feed stream from said fractional distillation column;
    means for removing a side draw stream containing normal butane from said fractional distillation column; and
    means for combining normal butane contained in said side draw stream with said feed stream flowing to said fractional distillation column to thereby recycle normal butane to said fractional distillation column as required to substantially minimize the presence of isobutane in said bottoms stream.

2. Apparatus in accordance with claim 1 additionally comprising:
    means for establishing a first signal representative of the actual alkylate to normal butane ratio in said bottoms stream;
    means for establishing a second signal representative of the alkylate to normal butane ratio in said bottoms stream required to substantially minimize the presence of isobutane in said bottoms stream;
    means for comparing said first signal and said second signal and for establishing a third signal which is responsive to the difference between said first signal and said second signal; and
    means for manipulating the recycling of normal butane to said fractional distillation column in response to said third signal to thereby insure that the actual alkylate to normal butane ratio in said bottoms stream does not go substantially below the desired ratio represented by said second signal.

3. Apparatus in accordance with claim 2 wherein said side draw stream is passed through a three-way control valve and split into first and second streams with said first stream being recycled to said fractional distillation column by combining said first stream with said feed stream and said second stream being removed as a normal butane product stream and wherein said means for manipulating the recycling of normal butane to said fractional distillation column in response to said third signal comprises:
    means for establishing a fourth signal which is representative of the actual flow rate of said first stream, wherein said third signal is scaled so as to be representative of the flow rate of said first stream required to insure that the actual alkylate to normal butane ratio in said bottoms product does not go substantially below the desired ratio represented by said second signal;
    means for comparing said third signal and said fourth signal and for establishing a fifth signal which is responsive to the difference between said third signal and said fourth signal, wherein said fifth signal is scaled so as to be representative of the position of said three-way control valve required to maintain the actual flow rate of said first stream substantially equal to the desired flow rate represented by said third signal; and
    means for manipulating said three-way control valve in response to said fifth signal.

4. A method for substantially minimizing the presence of isoparaffins in a bottoms stream withdrawn from a fractional distillation column, wherein a feed stream containing alkylate, isobutane and normal butane is supplied to said fractional distillation column, wherein a substantial portion of the alkylate contained in said feed stream is withdrawn from said fractional distillation column as said bottoms stream and wherein a side draw stream containing normal butane is withdrawn from said fractional distillation column, said method comprising the step of combining normal butane contained in said side draw stream with said feed stream flowing to said fractional distillation column to thereby recycle normal butane to said fractional distillation column as required to substantially minimize the presence of isobutane in said bottoms stream.

5. A method in accordance with claim 4 wherein said step of recycling normal butane contained in said side draw stream comprises:
    establishing a first signal representative of the actual alkylate to normal butane ratio in said bottoms stream;
    establishing a second signal representative of the alkylate to normal butane ratio in said bottoms stream required to substantially minimize the presence of isobutane in said bottoms stream;
    comparing said first signal and said second signal and establishing a third signal which is responsive to the difference between said first signal and said second signal; and
    manipulating the recycling of normal butane to said fractional distillation column in response to said third signal to thereby insure that the actual alkylate to normal butane ratio in said bottoms stream does not go substantially below the desired ratio represented by said second signal.

6. A method in accordance with claim 5 wherein said side draw stream is passed through a three-way control valve and split into first and second streams with said first stream being recycled to said fractional distillation column by combining said first stream with said feed stream and said second stream being removed as a normal butane product stream and wherein said step of manipulating the recycling of normal butane to said fractional distillation column in response to said third signal comprises:

establishing a fourth signal which is representative of the actual flow rate of said first stream, wherein said third signal is scaled so as to be representative of the flow rate of said first stream required to insure that the actual alkylate to normal butane ratio in said bottoms product does not go substantially below the desired ratio represented by said second signal;

comparing said third signal and said fourth signal and establishing a fifth signal which is responsive to the difference between said third signal and said fourth signal, wherein said fifth signal is scaled so as to be representative of the position of said three-way control valve required to maintain the actual flow rate of said first stream substantially equal to the desired flow rate represented by said third signal; and manipulating said three-way control valve in response to said fifth signal.

* * * * *